United States Patent [19]

Prindle et al.

[11] 4,252,725

[45] Feb. 24, 1981

[54] PREPARATION OF PHENOLPHTHALEIN USING CATION EXCHANGE RESINS AND ARYL PHOSPHITES

[75] Inventors: Hershel B. Prindle; George E. Ham, both of Lake Jackson, Tex.

[73] Assignee: The Dow Chemical Company, Midland, Mich.

[21] Appl. No.: 19,058

[22] Filed: Mar. 9, 1979

[51] Int. Cl.$^3$ ............................................. C07D 307/88
[52] U.S. Cl. ................................................... 260/343.4
[58] Field of Search ...................................... 260/343.4

[56] References Cited

U.S. PATENT DOCUMENTS 3,242,219   3/1966   Farnham ........................ 260/343.44

OTHER PUBLICATIONS

Yu, Tetrahedron Letters No. 60, pp. 5267–5270, 1969.
Sollazzo et al., La Chemica L'Industria 38:509 (1956).
Bilik et al., Chemical Abstracts 70:96355 1969.
Yamazaki et al., Tetrahedron Letters No. 49, pp. 5047–5050, 1972.

*Primary Examiner*—Henry R. Jiles
*Assistant Examiner*—Jane T. Fan
*Attorney, Agent, or Firm*—B. G. Colley

[57] ABSTRACT

A process for the preparation of phenol-phthalein wherein phenol and phthalic anhydride are reacted in the presence of a crosslinked sulfonic cation exchange resin in the acid form and wherein the water content of the reaction mixture is reduced by the use of aryl phosphites.

The sulfonic cation exchange resin can be in the macroporous form or in the gel form. The range of useful crosslinking is 4–40 percent for the macroporous resin and 2–16 percent for the gel resin.

16 Claims, No Drawings

PREPARATION OF PHENOLPHTHALEIN USING CATION EXCHANGE RESINS AND ARYL PHOSPHITES

BACKGROUND OF THE INVENTION

The process of this invention relates to a process for the preparation of phenolphthalein from phthalic anhydride and phenol in the presence of acid form cation exchange resins and aryl phosphites.

The use of Friedel-Crafts condensing agents such as, zinc chloride, tin chloride, sulfuric acid, benzene sulfonic acid and mixtures thereof is well known in the art for this condensation reaction as is illustrated by U.S. Pat. Nos. 1,381,503; 1,940,494; 1,995,402; 2,168,346; 2,192,485; 2,522,939; and 2,522,940.

Sollazzo, et al. in La Chemica L'Industria 38:509 (1956) showed that a mixture of zinc chloride and Amberlite IR 120 (a sulfonic cation exchange resin) could be used as a combined condensing agent to produce phenolphthalein.

It has been reported by Bilik, et al. Chemical Abstracts 70:96355 (1969) that sulfonic cation exchange resins alone can be used as a catalyst in the reaction. However, Bilik, et al. found the reaction to be very slow and gave poor yields, i.e., 40 hours reaction time and 18.6% yield.

In Ser. No. 750,786 filed Dec. 15, 1976, a process is disclosed wherein a cation exchange resin is used in conjunction with azeotropic distillation to produce phenolphthalein.

SUMMARY OF THE INVENTION

It now has been discovered that phenolphthalein can be produced by an improved process which eliminates the need for distillation columns and which gives generally higher conversions and generally faster reaction times by removing substantially all of the water during the reaction with an aryl phosphite.

The process of this invention comprises the steps of
(A) reacting one mole of phthalic anhydride or diphenyl phthalate with 2–20 moles of phenol and with 0.01 to 1 mole of an aryl phosphite to form a reaction mixture containing phenolphthalein, and by-products wherein the reaction is conducted at a temperature in the range from about 80° C. to about 140° C. in the presence of an effective amount of a sulfonic acid cation exchange resin in the acid form, and
(B) recovering phenolphthalein from the reaction mixture.

Preferably the molar range of phenol to phthalic anhydride or diphenyl phthalate is from about 4 to 12 and the molar range of phthalic anhydride or diphenyl phthalate to aryl phosphite is 0.02 to 0.5.

The sulfonic acid cation exchange resin used herein can be in a macroporous form in which case it is crosslinked to the extent of about 4 to about 40 percent and preferably in the range from about 6 to about 20 percent. The resin can also be used in the gel form wherein it is crosslinked to the extent of about 2 to about 16 percent and preferably in the range from about 4 to 10 percent.

In order to provide for the lowest water content present in the initial reaction mixture the additional step of drying the cation exchange resin prior to its use in the process may be employed. Drying may be accomplished by any conventional means such as oven drying, with a hot gas, with hot dry phenol, or by azeotropic distillation with phenol or other suitable azeotropic compounds.

In the process, the water content of the reaction mixture is reduced by the chemical reaction of the aryl phosphites to form more phenol.

The phenolphthalein may be recovered from the reaction mixture by filtering out the resin and removal of phenol by conventional methods such as distillation. The crude phenolphthalein obtained can be further purified by known methods such as recrystallization from methanol or ethanol.

The product of this process is suitable for pharmaceutical uses or to make aromatic condensation resins such as aromatic polyesters or aromatic polycarbonates.

DETAILED DESCRIPTION

The invention relates to a process wherein an excess of phenol is reacted with phthalic anhydride in the presence of an effective amount of a sulfonic acid cation exchange resin as the condensing agent.

For the purposes of this invention, an effective amount of the cation exchange resin is at least 10% by weight of the total reaction mixture and preferably the maximum amount of catalyst that can be in contact with the reaction mixture.

The macroporous cation exchange resins used herein are well known from U.S. Pat. Nos. 3,627,708; 3,586,646; and 3,367,889.

The gel type cation exchange resins are likewise well known from U.S. Pat. Nos. 2,500,149 and 2,366,007.

Examples of useful aryl phosphites are triaryl phosphites, alkyldiaryl phosphites and dialkylaryl phosphites. Specific examples are triphenyl phosphite, butyldiphenylphosphite, didecylphenyl phosphite, diisopropylphenylphosphite, and mixtures thereof.

The reaction of the phenol and phthalic anhydride or diphenylphthalate is conducted at a temperature range from 80° to 140° C. and preferrably in the range from 90° C. to 120° C.

The reaction times vary from 1 to 40 hours and are preferrably 2 to 8 hours. The following controls and examples are presented to illustrate and not limit the invention.

Control 1

A reaction mixture was prepared by heating 98.8 g (1.05 moles) phenol and 22.2 g (0.15 moles) phthalic anhydride on a hot plate with agitation until a clear yellow solution was obtained. The hot solution was slowly added to a jacketed column (15 inches long by ½" diameter) packed with Dowex MSC-1 sulfonic acid cation exchange resin beads in the acid form. The resin was swollen with phenol before the reaction was started. The column was indirectly heated by a directing a refluxing liquid (1-methoxy-2-propanol) through the jacket. The first liquid that came out of the column was phenol. As soon as an amount of feed had been added that was equivalent to the void volumn of column, phenolphthalein started eluding. After 2.5 hours of reaction at 120° C., the average conversion at equilibrium conditions was 13.1%.

EXAMPLE 1

This run was carried out exactly as in Control 1 except the following charge was used.

98.9 g Phenol (1.05 Moles) 22.2 g Phthalic anhydride (0.15 Moles)

9.3 g Triphenyl Phosphite (0.03 Moles)

After equilibrium had been established, the average conversion was 19.0%.

Control 2

This run was similar to Control 1 except the following charge was used.

98.9 g Phenol (1.05 Moles) 47.4 g Diphenyl Phthalate (0.15 Moles)

After equilibrium had been established the average conversion was 30.1%.

EXAMPLE 2

This run is identical to Control 2 except 9.3 g (0.03 Moles) triphenyl phosphite was added to the charge. After equilibrium the averge conversion was 36.9%.

The results of these runs are set forth in Table I below:

TABLE I

| | Moles Reactants | | | |
|---|---|---|---|---|
| Run | Phenol | Phthalic Anhydride | Diphenyl Phthalate | Triphenyl Phosphite | Percent Conversion |
| Cont. 1 | 7 | 1 | — | 0 | 13.1 |
| Exam. 1 | 7 | 1 | — | .3 | 19.0 |
| Cont. 2 | 7 | — | 1 | 0 | 30.1 |
| Exam. 2 | 7 | — | 1 | .3 | 36.9 |

It is seen from Table I that higher conversions are obtained in both cases where triphenyl phosphite is incorporated into the change.

Results similar to the Examples 1 and 2 above are obtained when diphenyl phosphite and phenyl phosphite are used in place of triphenyl phosphite.

We claim:

1. A process for producing phenolphthalein which comprises the steps of
   (A) reacting one mole of phthalic anhydride or diphenyl phthalate with 2–20 moles of phenol and with 0.01 to 1 mole of an aryl phosphite to form a reaction mixture containing phenolphthalein, and by-products wherein the reaction is conducted at a temperature in the range from about 80° C. to about 140° C. in the presence of an effective amount of a sulfonic acid cation exchange resin in the acid form, and
   (B) recovering phenolphthalein from the reaction mixture.

2. The process as set forth in claim 1 wherein the range of phenol is from about 4 to about 12 moles.

3. The process as set forth in claim 1 wherein the crosslinked sulfonic acid cation exchange resin is macroporous and crosslinked from about 4 to about 40 percent.

4. The process as set forth in claim 1 wherein the crosslinked sulfonic acid cation exchange resin is a gel resin crosslinked to the extent of about 2 to about 16 percent.

5. The process of claim 1 wherein the aryl phosphite is a tri aryl phosphite.

6. The process of claim 1 wherein the aryl phosphite is a di aryl phosphite.

7. The process of claim 1 wherein the aryl phosphite is a mono aryl phosphite.

8. The process of claim 5 wherein the tri aryl phosphite is triphenyl phosphite.

9. In a process of producing phenolphthalein wherein one mole of phthalic anhydride or diphenyl phthalate is reacted with 2–20 moles of phenol to form a reaction mixture containing phenolphthalein, and by-products wherein the reaction is conducted at a temperature in the range from about 80° C. to about 140° C. in the presence of an effective amount of sulfonic acid cation exchange resin in the acid form, and the phenolphthalein is recovered from the reaction mixture, the improvement which comprises carrying out the reaction in the presence of 0.01 to 1 mole of an aryl phosphite.

10. The process as set forth in claim 9 wherein the range of phenol is from about 4 to about 12 moles.

11. The process as set forth in claim 9 wherein the crosslinked sulfonic acid cation exchange resin is macroporous and crosslinked from about 4 to about 40 percent.

12. The process as set forth in claim 9 wherein the crosslinked sulfonic acid cation exchange resin is a gel resin crosslinked to the extent of about 2 to about 16 percent.

13. The process of claim 9 wherein the aryl phosphite is a tri aryl phosphite.

14. The process of claim 9 wherein the aryl phosphite is di aryl phosphite.

15. The process of claim 9 wherein the aryl phosphite is a mono aryl phosphite.

16. The process of claim 13 wherein the tri aryl phosphite is triphenyl phosphite.

* * * * *